United States Patent
Su et al.

(10) Patent No.: US 11,842,426 B2
(45) Date of Patent: Dec. 12, 2023

(54) METHODS FOR DETERMINING A FITTING MODEL FOR A SIGNAL, RECONSTRUCTING A SIGNAL AND DEVICES THEREOF

(71) Applicant: Raycan Technology Co., Ltd. (Suzhou), Suzhou (CN)

(72) Inventors: Yuming Su, Suzhou (CN); Junhua Mei, Suzhou (CN); Kezhang Zhu, Suzhou (CN); Qingguo Xie, Suzhou (CN); Pingping Dai, Suzhou (CN); Hao Wang, Suzhou (CN)

(73) Assignee: Raycan Technology Co., Ltd. (Suzhou), Jiangsu (CN)

( * ) Notice: Subject to any disclaimer, the term of this patent is extended or adjusted under 35 U.S.C. 154(b) by 472 days.

(21) Appl. No.: 17/256,873

(22) PCT Filed: May 9, 2019

(86) PCT No.: PCT/CN2019/086237
§ 371 (c)(1),
(2) Date: Dec. 29, 2020

(87) PCT Pub. No.: WO2020/042663
PCT Pub. Date: Mar. 5, 2020

(65) Prior Publication Data
US 2021/0275113 A1    Sep. 9, 2021

(30) Foreign Application Priority Data
Aug. 27, 2018   (CN) .......................... 201810983248.2

(51) Int. Cl.
*G06T 11/00*       (2006.01)
*A61B 6/03*        (2006.01)
*A61B 6/00*        (2006.01)

(52) U.S. Cl.
CPC ............ *G06T 11/005* (2013.01); *A61B 6/037* (2013.01); *A61B 6/5211* (2013.01)

(58) Field of Classification Search
CPC ...... G06T 11/005; A61B 6/037; A61B 6/5211
See application file for complete search history.

(56) References Cited

U.S. PATENT DOCUMENTS 9,772,408 B2 *   9/2017   Xie .......................... G01T 1/17
9,922,003 B2     3/2018   Manton et al.
(Continued)

FOREIGN PATENT DOCUMENTS

CN       102262238 A       11/2011
CN       103814273 A        5/2014
(Continued)

OTHER PUBLICATIONS

Kim, Heejong, et al. "A multi-threshold sampling method for TOF-PET signal processing." Nuclear Instruments and Methods in Physics Research Section A: Accelerators, Spectrometers, Detectors and Associated Equipment 602.2 (2009): 618-621. (Year: 2009).*
(Continued)

*Primary Examiner* — Utpal D Shah
(74) *Attorney, Agent, or Firm* — Shumaker & Sieffert, P.A.

(57) ABSTRACT

The disclosure discloses methods for determining fitting model for a signal, reconstructing a signal and devices thereof. The determination method may comprise the following steps: segmenting a sampled signal based on collected characteristic information of the signal to obtain a plurality of signal segments; fitting sampling points in the plurality of signal segments using a plurality of fitting models; acquiring fitted values for a parameter of interest in each signal segment based on fitting results; comparing each of the fitted values for the parameter of interest under each
(Continued)

of the fitting models with an acquired measurement value for the parameter of interest, and determining a final fitting model for reconstructing the signal among the plurality of the fitting models based on comparison results. In the technical solution provided in the disclosure, the accuracy of the signal reconstruction result and precision of the signal reconstruction may be improved.

19 Claims, 10 Drawing Sheets

(56) References Cited

U.S. PATENT DOCUMENTS

| | | | |
|---|---|---|---|
| 2014/0052414 A1* | 2/2014 | Xie | G01T 1/2006 702/189 |
| 2016/0199033 A1 | 7/2016 | Yeh | |
| 2016/0216386 A1 | 7/2016 | Moskal | |

FOREIGN PATENT DOCUMENTS

| | | |
|---|---|---|
| CN | 103969675 A | 8/2014 |
| CN | 104146726 A | 11/2014 |
| CN | 105588667 A | 5/2016 |
| CN | 107024711 A | 8/2017 |
| CN | 108021535 A | 5/2018 |
| EP | 3098780 A1 | 11/2016 |
| EP | 3614181 A1 | 2/2020 |

OTHER PUBLICATIONS

Xie, Qingguo, et al. "Potentials of digitally sampling scintillation pulses in timing determination in PET." IEEE transactions on nuclear science 56.5 (2009): 2607-2613. (Year: 2009).*
International Search Report dated Jul. 26, 2019 from counterpart International Application No. PCT/CN2019/086237, 8 pp.
Mou, Wanjun et al., "HPGe γ, (Fitting of Efficiency Curves for HPGe y Spectrometer)," Radiation Protection Bulletin, vol. 29, No. 6, Dec. 21, 2009, ISSN: 1004-6356, pp. 35-37.
Ren, Shuhong et al., "Non-official translation: Comparative Study of Different Fitting Methods Based on Natural Law of Data," Management & Technology of SME (First issue of a month), No. 2, Feb. 28, 2017, ISSN: 1673-1069, sections 3.1, 3.3 and 3.5, 3 pages.
Chinese Office Action for corresponding CN Application No. 201810983248.2, dated Dec. 24, 2019, 10 pages.
Chinese Office Action for corresponding CN Application No. 201810983248.2, dated Aug. 21, 2020, 9 pages.

* cited by examiner

```
┌─────────────────────────────────────────────────────────────────┐
│ Segmenting a sampled signal based on collected characteristic   │
│ information of the signal to obtain a plurality of signal       │──S1
│ segments                                                        │
└─────────────────────────────────────────────────────────────────┘
                                 ↓
┌─────────────────────────────────────────────────────────────────┐
│ Fitting sampling points in the plurality of signal segments by  │──S2
│ using a plurality of fitting models                             │
└─────────────────────────────────────────────────────────────────┘
                                 ↓
┌─────────────────────────────────────────────────────────────────┐
│ Acquiring fitted values for a parameter of interest in each of  │──S3
│ the signal segments based on fitting results                    │
└─────────────────────────────────────────────────────────────────┘
                                 ↓
┌─────────────────────────────────────────────────────────────────┐
│ Sequentially comparing each of the fitted values for the        │
│ parameter of interest under each of the fitting models with an  │
│ acquired measurement value for the parameter of interest, and   │──S4
│ determining a final fitting model for reconstructing the signal │
│ among the plurality of the fitting models according to          │
│ comparison results                                              │
└─────────────────────────────────────────────────────────────────┘
```

FIG. 2

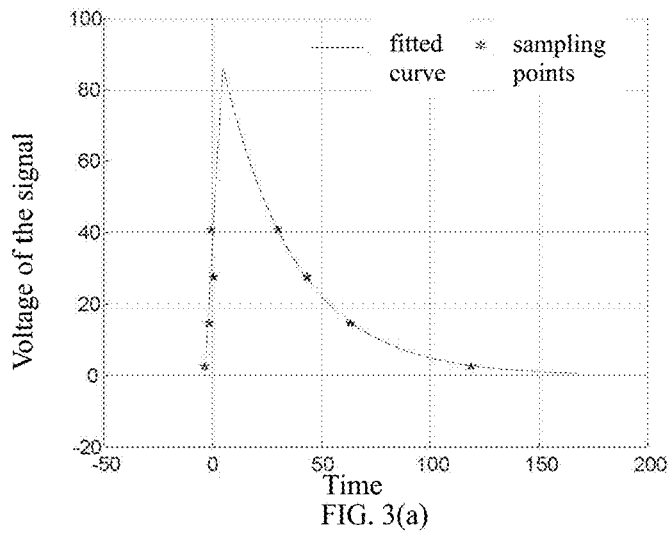

FIG. 3(a)

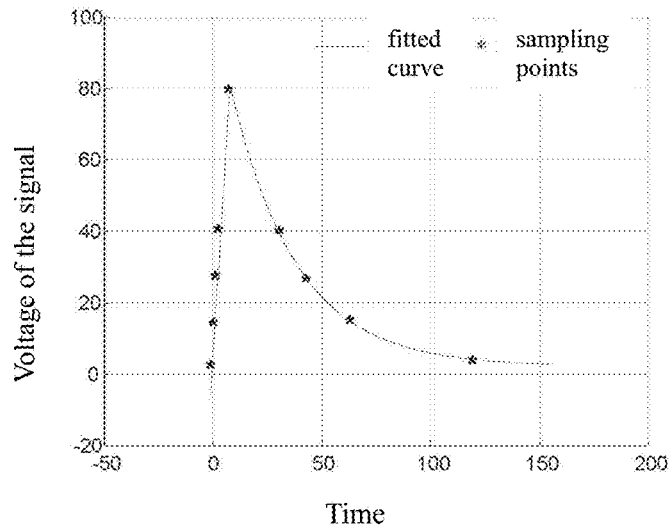

FIG. 3(b)

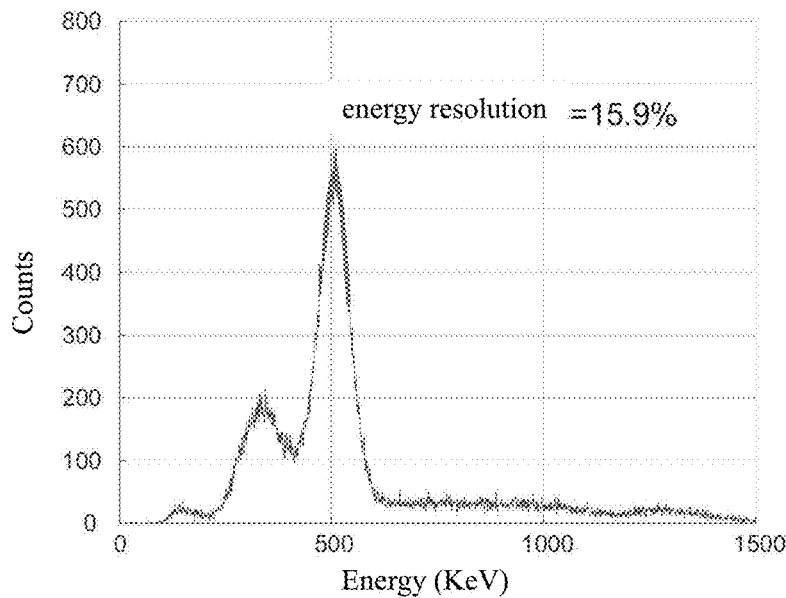
FIG. 10
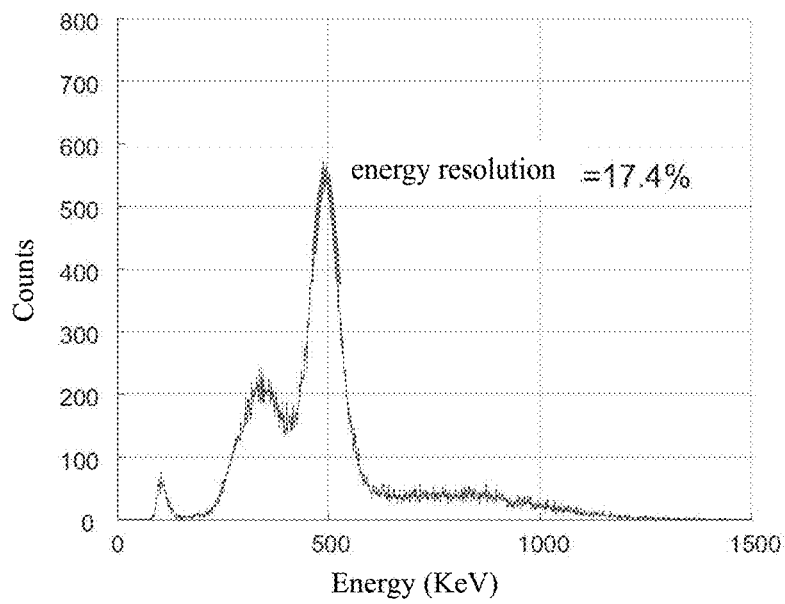
FIG. 11
Comparing an actually sampled signal with a reference signal, a final fitting model for which is determined by utilizing the above determination method, to determine a final fitting model for the actually sampled signal — P1'
Reconstructing the actually sampled signal by utilizing the determined final fitting model — P2'
FIG. 12

METHODS FOR DETERMINING A FITTING MODEL FOR A SIGNAL, RECONSTRUCTING A SIGNAL AND DEVICES THEREOF

This application is a national stage application under 35 U.S.C. § 371 of PCT Application No. PCT/CN2019/086237, filed May 9, 2019, which claims the benefit of China Application No. 201810983248.2, filed Aug. 27, 2018. The entire contents of each of PCT Application No. PCT/CN2019/086237 and China Application No. 201810983248.2 are incorporated herein by reference in their entireties.

TECHNICAL FIELD

This disclosure relates to the technical field of signal processing, and in particular to methods for determining a fitting model for a signal, reconstructing a signal and devices thereof.

BACKGROUND

The description in this section only provides background information related to the disclosure, and does not constitute prior art.

Positron Emission Tomography (abbr. PET) is a technique that uses radioactive elements for clinical imaging. The processes of this technique include: labeling the positron-emitting radionuclides into a compound that is able to be added in the blood flow or participate in the metabolic process of living tissues, and then injecting the compound labeled with the radionuclides into a subject. Positrons emitted by the radionuclides in the subject's body moves about 1 mm and then combines with negative electrons in the subject's body to annihilate electron pairs, and thus generate gamma photons, which can be received by the scintillation crystal and converted into visible light, which in turn are converted into electrical signals by the photoelectric converter for reconstruction, thereby helping to determine the enrichment site of the radionuclides, locate the area of vigorous metabolism and evaluate the activity of the radionuclides.

In PET or other related fields, in order to reconstruct a signal, it is necessary to perform fitting processing on the sampling points of the signal after sampling. In the prior art, the fitting model for fitting the sampling points is selected mainly based on experience or scatter plots. Specifically, for each sampling point, various scatter plots of all sampling points may be drawn under various fitting models by taking the measurement value of a parameter of interest of the signal as the abscissa value and taking the fitted value of the parameter of interest obtained by fitting the sampling points under the various fitting models as the ordinate value, as shown in FIG. 1(a) to FIG. 1(c). The fitting model is selected by observing the dispersion degree and linearity among the scattered points in the scatter plot.

SUMMARY

In the process of realizing this disclosure, the inventors found at least the following problems in the prior art:

In the prior art, although the signal parameters and the fitted curve parameters can be intuitively observed through the scatter plots, the dispersion degree of the scatter points is difficult to be measured and an intuitive conclusion is often obtained just by an observation method. As a result, subsequent reconstruction results may not be accurate enough, which will affect the precision of signal reconstruction.

The purpose of this disclosure is to provide methods for determining a fitting model for a signal, reconstructing a signal and devices thereof, so as to improve the accuracy of the signal reconstruction results and the precision of the signal reconstruction.

To achieve the above object, in the embodiments of the disclosure, the following technical solutions are provided:

A method for determining a fitting model for a signal, comprising:

segmenting a sampled signal based on collected characteristic information of the signal to obtain a plurality of signal segments;

fitting sampling points in the plurality of signal segments by using a plurality of fitting models;

acquiring fitted values for a parameter of interest in each of the signal segments based on fitting results;

sequentially comparing each of the fitted values for the parameter of interest under each of the fitting models with an acquired measurement value for the parameter of interest, and determining a final fitting model for reconstructing the signal among the plurality of the fitting models based on comparison results.

Preferably, the signal includes an electrical signal, an optical signal or a sound signal. The electrical signal includes an electrical pulse signal from a radiation detector.

Preferably, the characteristic information includes amplitude, rising slope, rising time, falling slope and/or falling time of the signal.

Preferably, the plurality of the fitting models comprises: at least one of linear-exponential fitting model, double exponential fitting model and graph fitting model.

Preferably, the graph fitting model comprises a triangle fitting model adopted at an upper portion with respect to a sampling threshold, and the linear exponential fitting model or the double exponential fitting model adopted at a lower portion with respect to the sampling threshold. The linear exponential fitting model includes an N-point linear-N-point exponential fitting model or an N-point linear-N-plus-M-point exponential fitting model. The double exponential fitting model includes a 2N-point double exponential fitting model or a 2N-plus-M-point double exponential fitting model, wherein N is a positive integer greater than 1 and M is a positive integer greater than or equal to 1.

Preferably, the parameter of interest includes energy, time, energy resolution and/or time resolution of the signal.

Preferably, the step of determining the final fitting model includes:

sequentially calculating difference value between each of the fitted values of the parameter of interest in each of the signal segments under each of the fitting models and the acquired measurement value for the parameter of interest, and determining the final fitting model for reconstructing each of the signal segments among the plurality of the fitting models based on the difference value.

Preferably, the step of determining the final fitting model includes:

determining, among the plurality of the fitting models, a fitting model under which there is a smallest absolute difference value for the parameter of interest in each of the signal segments, as the final fitting model for each of the signal segments; or determining, among the plurality of the fitting models, a fitting model under which there is a smallest difference distribution for the parameter of interest in each of the signal segments, as the final fitting model for each of the signal segments.

Preferably, the method further includes:

storing the final fitting model according to the correspondence between the final fitting model and each of the signal segments.

A method for reconstructing a signal method, including the following steps:

determining a final fitting model for an actually sampled signal by utilizing the above method; and reconstructing the actually sampled signal by utilizing the determined final fitting model.

A method for reconstructing a signal, including the following steps:

comparing an actually sampled signal with a reference signal, a final fitting model for which is determined by utilizing the above method, to determine a final fitting model for the actually sampled signal; and reconstructing the actually sampled signal by utilizing the determined final fitting model.

Preferably, the step of comparing the actually sampled signal with the reference signal includes:

searching for the reference signal having same or similar characteristic information with the actually sampled signal by utilizing characteristic information of the actually sampled signal; and after the reference signal is searched out, searching for the final fitting model for the reference signal according to the correspondence between the reference signal and the final fitting model, and determining the searched final fitting model for the reference signal as the final fitting model for the actually sampled signal.

A device for determining a signal fitting model, including:

a segmentation unit configured to segment a sampled signal based on collected characteristic information of the signal to obtain a plurality of signal segments;

a fitting unit configured to fit sampling points in the plurality of signal segments by using a plurality of fitting models;

an acquisition unit configured to acquire fitted values for a parameter of interest in each of the signal segments based on fitting results; and a comparison and determination unit configured to compare each of the fitted values for the parameter of interest under each of the fitting models with an acquired measurement value for the parameter of interest, and to determine a final fitting model for reconstructing the signal among the plurality of the fitting models based on comparison results.

Preferably, the comparison and determination unit may be specifically configured to:

sequentially calculate difference value between each of the fitted values for the parameter of interest in each of the signal segments under each of the fitting models and the acquired measurement value for the parameter of interest, and determining the final fitting model for reconstructing each of the signal segments among the plurality of the fitting models based on the difference value.

Preferably, the device further includes:

a storage unit configured to store the final fitting model according to the correspondence between the final fitting model and each of the signal segments.

A device for reconstructing a signal, including:

a determination unit configured to determine a final fitting model for an actually sampled signal by utilizing the above method; and a reconstruction unit configured to reconstruct the actually sampled signal by utilizing the determined final fitting model.

A device for reconstructing a signal, including:

a comparison and determination unit configured to compare an actually sampled signal with a reference signal, the final fitting model for which is determined by utilizing the above method, to determine a final fitting model for the actually sampled signal; and a reconstruction unit configured to reconstruct the actually sampled signal by utilizing the determined final fitting model.

Preferably, the comparison and determination unit is specifically configured to search for the reference signal having the same or similar characteristic information with the actually sampled signal by utilizing characteristic information of the actually sampled signal, and after the reference signal is searched out, to search for the final fitting model for the reference signal according to the correspondence between the reference signal and the final fitting model, and to determine the searched final fitting model for the reference signal as the final fitting model for the actually sampled signal.

It can be seen from the technical solutions provided by the above embodiments of the present disclosure, the sampled signal is segmented according to the characteristic information of the signal, and the fitted values of the parameter of interest of the signal obtained by using a plurality of fitting models are compared with the measurement value, such that the final fitting model is determined according to the comparison results. By adopting different fitting models by considering different characteristics of the signal, subsequent fitting results of the signal may be more accurate, and thus the purpose for improving accuracy of the signal reconstruction result and precision of the signal reconstruction can be achieved.

BRIEF DESCRIPTION OF THE DRAWINGS

In order to describe the technical solution in the embodiments of the disclosure or the prior art more clearly, accompanying drawings required to be used in the description of the embodiments or the prior art will be introduced briefly as follows. It is apparent that the drawings as shown are merely illustrative of some embodiments as recited in the disclosure. It should be understood by those skilled in the art that various alternatives to the drawings as shown may be appreciated, without creative work involved.

FIG. 2 is a schematic flowchart of a method for determining a fitting model for a signal according to an embodiment of the disclosure;

FIG. 3(a) is the fitted curve obtained by fitting the sampling points using an N-point linear and N-point exponential fitting model;

FIG. 3(b) is the fitted curve obtained by fitting the sampling points using an N-point linear and N-plus-M-point exponential fitting model;

FIG. 10 shows a fitted curve obtained by using the method for reconstructing the signal in FIG. 7;

FIG. 11 shows a fitted curve obtained by using an existing multi-threshold sampling method;

FIG. 12 is a schematic flowchart of another method for reconstructing a signal according to an embodiment of the disclosure;

DETAILED DESCRIPTION

Figure 1A:
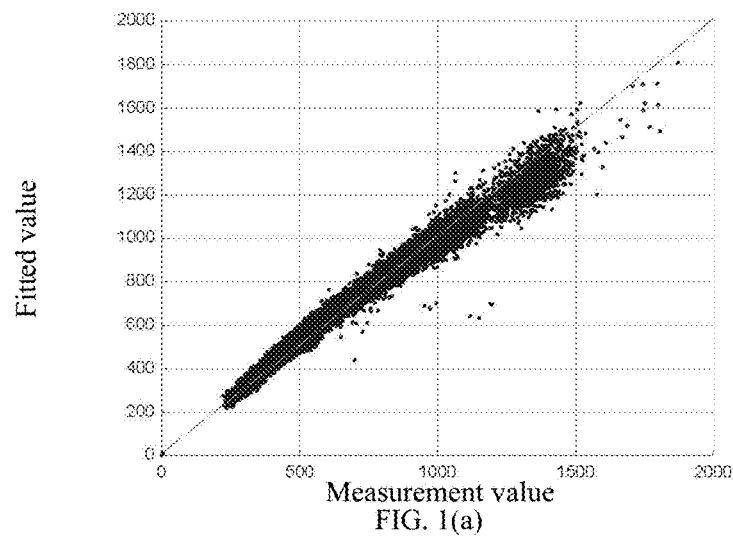
FIG. 1(a) is a scatter plot, in which sampling points are fitted using a four-point linear and five-point exponential fitting model in the prior art.
Figure 1B:
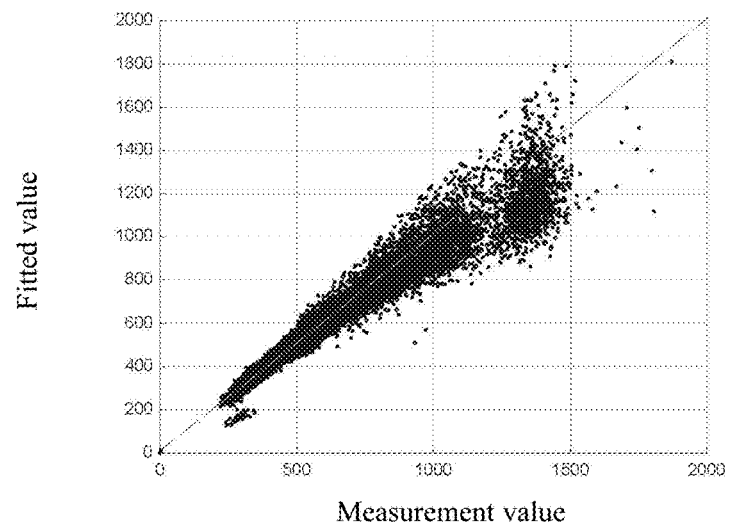
FIG. 1(b) is a scatter plot, in which sampling points are fitted using an eight-point double exponential fitting model in the prior art.
Figure 1C:
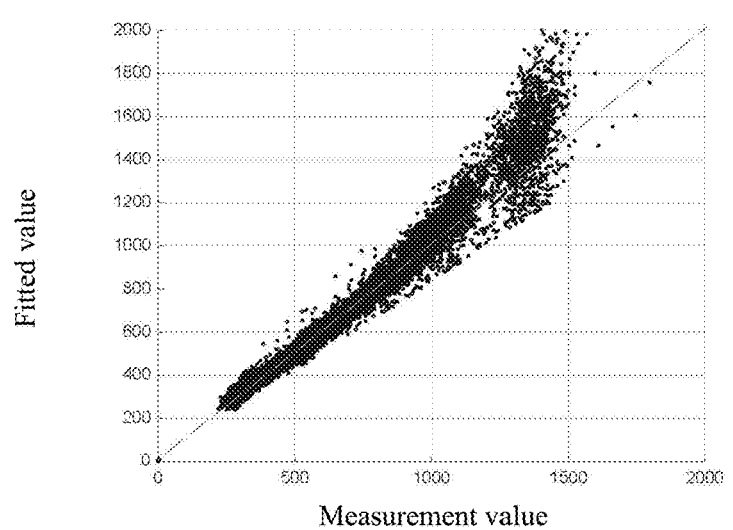
FIG. 1(c) is a scatter plot, in which sampling points are fitted using a graph fitting model in the prior art.

The technical solutions in the embodiments of the disclosure will be clearly and comprehensively described in the following description with reference to the accompanying drawings. It is apparent that the described embodiments are only provided to illustrate some exemplary embodiments of the disclosure, rather than exhaustively elaborate all of them, which shall not be construed to limit the scope of the disclosure or the claims. It should be understood that various alternatives to the embodiments described herein may be employed by those skilled in the art without creative work involved and without departing from the scope of the disclosure.

Notably, when an element is referred to as being "disposed on" another element, it can be directly disposed on another element or there may be an intermediate element. When an element is referred to as being "connected or coupled" to another element, it may be directly connected or coupled to another element or there is an intermediate element. The term "connection or coupling" used herein may include electrical connection or coupling and/or mechanical or physical connection or coupling. The term "comprise or include" used herein refers to the existence of features, steps or elements, but does not exclude the existence or addition of one or more other features, steps or elements. The term "and/or" used herein includes any and all combinations of one or more of the related listed items. The terms "a", "an", "one", "the" and other similar terms include both singular and plural forms, unless context clearly dictates otherwise.

Unless otherwise indicated, all the technical and scientific terms used herein have general meaning as commonly understood by those skilled in the technical field related to the disclosure. The terms used herein are for the purpose of describing specific embodiments, but not intended to limit the disclosure.

In addition, the terms "first", "second", "third" or the like used herein are only for the purpose of description and to distinguish similar objects from each other, which do not express the sequence thereof, nor can they be understood as indication or implication of relative importance. In addition, unless otherwise specified, "a plurality of" used herein means two or more.

Hereinafter, a method for determining a fitting model for a signal, a method for reconstructing a signal, and devices thereof according to the embodiments of the disclosure will be described in detail with reference to the accompanying drawings.

As shown in FIG. 2, in an embodiment of the disclosure, a method for determining a fitting model for a signal is provided, which comprises the following steps:

Step S1: segmenting a sampled signal based on collected characteristic information of the signal to obtain a plurality of signal segments.

After sampling a signal, the signal may be segmented based on the collected characteristic information of the signal. Specifically, the sampled signal may be segmented into the plurality of signal segments based on the amplitude (i.e., amplitude value), rising slope, rising time, falling slope, and/or falling time of the signal, etc. For example, the signal may be segmented into the plurality of signal segments, such as 0-M1, M1-M2, M2-M3, Mk-Mn, and >Mn, etc., based on the amplitude. For another example, the signal may be segmented into the plurality of signal segments, such as 0-T1, T1-T2, T2-T3, Ti-Tj, and >Tj, etc., based on the time. Wherein, M1, M2, M3, Mk and Mn represent different amplitudes of the signal (such as voltage or current or the like), and T1, T2, T3, Ti and Tj represent different time values of the signal. It should be noted that the interval of each signal segment may be the same or different.

The signal may be an electrical signal, an optical signal, a sound signal or the like. The signal may be same one signal from the same device or various signals from different devices. The electrical signal may include an electrical pulse signal from radiation detectors such as scintillation crystal detectors or gas ionization detectors.

The characteristic information may be the data obtained from the sampled result of the signal. The characteristic information may include amplitude, rising slope, rising time, falling slope and/or falling time of the signal, etc.

S2: fitting sampling points in the plurality of signal segments by using a plurality of fitting models.

After the signal is segmented, a plurality of fitting models may be used to fit the sampling points in each signal segment to obtain the fitted curve of the complete signal under the plurality of the fitting models, thereby obtaining a reconstructed waveform of the signal.

The fitting models may include, but are not limited to at least one type of linear and exponential fitting model, double exponential fitting model and graph fitting model, etc. The graph fitting model may include, but is not limited to a triangle fitting model adopted at an upper portion with respect to a sampling threshold, and the linear and exponential fitting model or the double exponential fitting model adopted at a lower portion with respect to the sampling threshold. The linear and exponential fitting model may include, but is not limited to an N-point linear and N-point exponential fitting model or an N-point linear and N-plus-M-point exponential fitting model, etc. The double exponential fitting model may include, but is not limited to a 2N-point double exponential fitting model or a 2N-plus-M-point double exponential fitting model, etc. Wherein, N represents the number of sampling points on the rising edge portion or the falling edge portion obtained by sampling the signal by the multi-threshold sampling method, which is a positive integer greater than 1; and M represents the number of sampling points further obtained by sampling the signal according to time intervals on the basis of sampling the signal by the multi-threshold method, which is a positive integer greater than or equal to 1. Reference may be made to the prior art with respect to the specific process of multi-threshold sampling method and time interval sampling method, which will not be elaborated here.

N-point linear and N-point exponential fitting model: Exclusive of the sampling point with the greatest amplitude, the N sampling points on the rising edge portion of the signal, which are taken as reference points, are fitted to generate a straight line; the N sampling points on the falling edge portion of the signal, which are taken as reference points, are fitted to generate an exponential curve according to the exponential curve equation, and thus the generated straight line and exponential curve constitute the reconstructed waveform of the signal, as shown in FIG. 3(a), wherein, N=4.

N-point linear and N-plus-M-point exponential fitting model: The N sampling points on the rising edge portion of the signal, which are taken as reference points, are fitted to generate a straight line; the N sampling points and the M sampling points on the falling edge portion of the signal, which are taken as reference points, are fitted to generate an exponential curve according to the exponential curve equation, and thus the generated straight line and exponential curve constitute the reconstructed waveform of the signal, as shown in FIG. 3(b), wherein, N=4 and M=1.

Figure 3C:
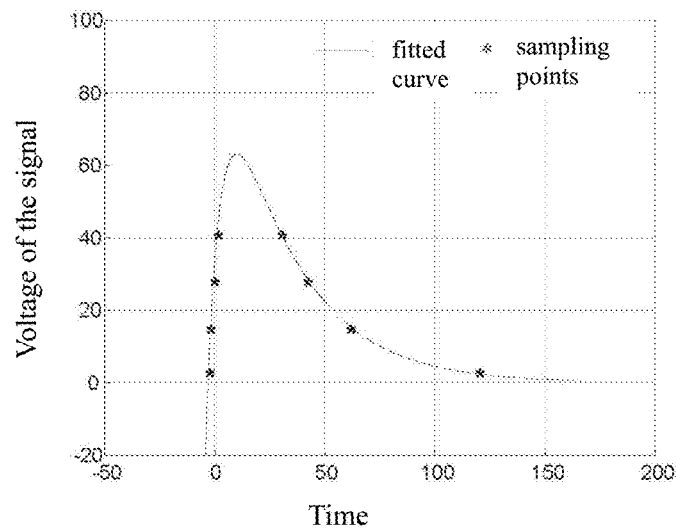
FIG. 3(c) is the fitted curve obtained by fitting the sampling points using a 2N-point double exponential fitting model.

2N-point double exponential fitting model: The 2N sampling points obtained by performing multi-threshold sampling on the signal, which are taken as reference points, are fitted to generate a double exponential curve according to the double exponential curve equation, and thus the obtained double exponential curve constitutes the reconstructed waveform of the signal, as shown in FIG. 3(c), wherein, N=4.

Figure 3D:
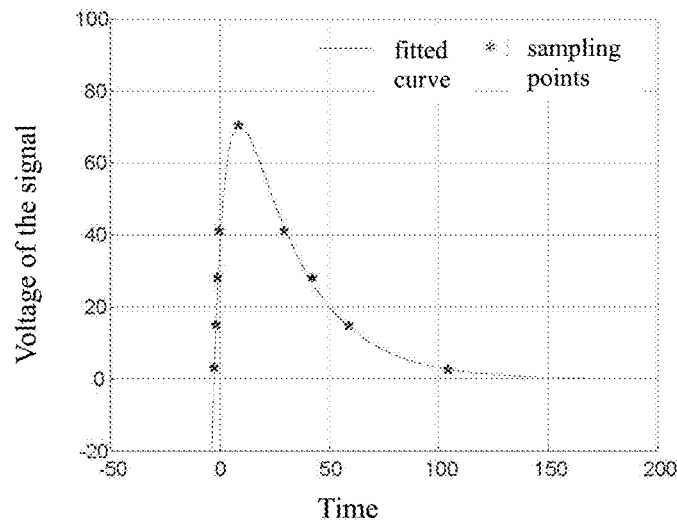
FIG. 3(d) is the fitted curve obtained by fitting the sampling points using a 2N-plus-M-point double exponential fitting model.

2N-plus-M-point double exponential fitting model: The 2N sampling points obtained by performing multi-threshold sampling on the signal and the M sampling points obtained by sampling the signal at time intervals, which are taken as the reference points, are fitted to generate a double exponential curve according to the double exponential curve equation, and thus the obtained double exponential curve constitutes the reconstructed waveform of the signal, as shown in FIG. 3(d), wherein, N=4 and M=1.

Figure 3E:
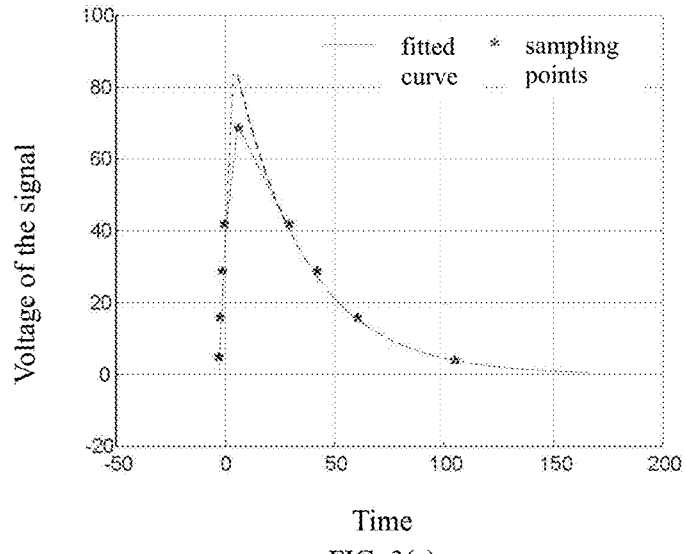
FIG. 3(e) is the fitted curve obtained by fitting the sampling points using graph fitting model, in which the lower curve is fitted by N-point linear and N-plus-M-point exponential fitting model.
Figure 3F:
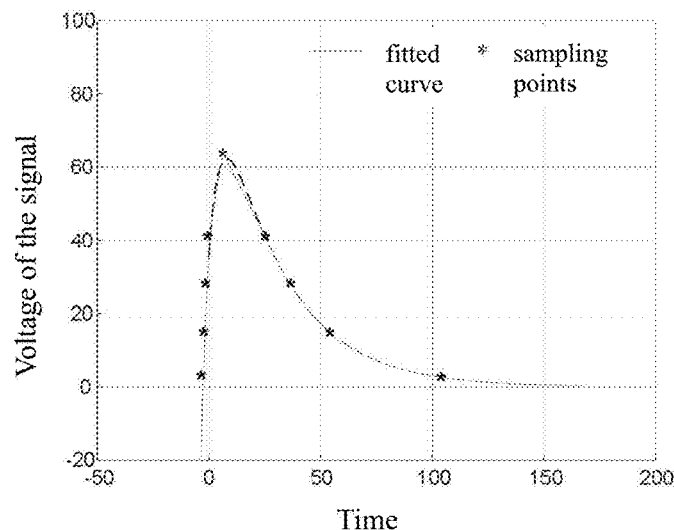
FIG. 3(f) is the fitted curve obtained by fitting the sampling points using graph fitting model, in which the lower curve is fitted by 2N-point double exponential fitting model.

Graph fitting model: The sampled 2N+M sampling points are taken as the reference points, and in an upper portion with respect to a certain sampling threshold, such as the maximum sampling threshold of the signal, three sampling points, such as the last sampling point on the rising edge portion, the sampling point at the peak, and the first sampling point on the falling edge portion (where "first" and "last" are indicated chronologically) are connected with each other with straight lines to form a triangle, and in a lower portion with respect to the sampling threshold of the signal, the sampling points are fitted according to a linear and exponential or double-exponential fitting model, etc., so as to obtain a complete signal reconstruction waveform, as shown in FIGS. 3(e) and 3(f). Wherein, in FIG. 3(e), the signal in the lower portion with respect to the maximum sampling threshold is fitted according to the linear and exponential mode, and in FIG. 3(f), the signal in the lower portion with respect to the maximum sampling threshold is fitted according to the double exponential fitting model.

S3: acquiring fitted values for a parameter of interest in each of the signal segments based on fitting results.

After using various fitting models to fit all the sampling points in all the signal segments, the fitting value for the parameter of interest at each sampling point in each signal segment may be directly obtained from the obtained fitting results, or may also be obtained by calculating the data obtained from the fitting results.

The fitting results may be fitted curves and/or fitting data.

The parameter of interest may refer to a parameter that needs to be considered according to practical applications, which may include, but is not limited to, energy, time, and/or energy resolution of the signal, etc. Wherein, the energy resolution may refer to the ratio of the half-width of the all-power peak to the expected value of the energy of the all-power peak of the signal energy spectrum, representing the ability to distinguish the signal energy intervals from each other, and the lower the energy resolution is, the stronger the ability to distinguish the energy intervals in the energy spectrum from each other is.

When the parameter of interest is time, the time value, i.e., fitted value may be extracted directly from the obtained fitted curve. When the parameter of interest is energy, the fitted value may be obtained by processing the extracted amplitude, such as voltage or current. For example, the energy can be obtained by integrating the voltage amplitude, and the specific calculation process thereof may refer to the prior art, which will not be elaborated here.

Likewise, when the parameter of interest is energy resolution or the like, the fitted value may be obtained by processing the extracted time or amplitude, the specific process of which is not limited here.

S4: Sequentially comparing each of the fitted values for the parameter of interest under each of the fitting models with an acquired measurement value for the parameter of interest, and determining a final fitting model for reconstructing the signal among the plurality of the fitting models according to comparison results.

After obtaining the fitted values for the parameter of interest at all the sampling points in all the signal segments under each fitting model, each of the fitted values for the parameter of interest at each sampling point in each signal segment under each fitting model may be sequentially compared with the measurement value (i.e., the true value) of the parameter of interest at the sampling point. Then the final fitting model for reconstructing the signal among the plurality of the fitting models may be determined according to the comparison results. Specifically, for each signal, it may directly compare magnitude of the fitted value for the parameter of interest at each sampling point in each signal segment under each fitting model with magnitude of the corresponding measurement value, or it may calculate the difference value between the fitted value for the parameter of interest at each sampling point in each signal segment under each fitting model and the corresponding measurement value; and then it may determine the final fitting model for reconstructing the signal among the plurality of the fitting models according to the difference value.

Specifically, for each signal, it may firstly sequentially calculate the difference value between the fitted value for the parameter of interest at each sampling point in each signal segment under each fitting model and the corresponding measurement value in a preset order, for example, in an increasing order of the magnitudes of abscissa or ordinate values of the sampling points. For example, in the situation where the parameter of interest is energy, it may sequentially calculate the difference value between the fitted value for energy at each sampling point in each signal segment under each fitting model and the corresponding measurement value. Secondly, after calculating all the difference values for the parameter of interest, it may determine the final fitting model for reconstructing each of the signal segments based on the difference values. Specifically, it may determine, among the plurality of the fitting models, the fitting model under which there is a smallest absolute difference value for the parameter of interest in each signal segment, as the final fitting model for the respective signal segment. Alternatively, it may determine, among the plurality of the fitting models, the fitting model under which there is a smallest difference distribution for the parameter of interest in each of the signal segments, as the final fitting model for the respective signal segment in accordance with the following manners, so as to determine all the final fitting models for all the signal segments:

For each fitting model and each signal, a matrix of n rows multiplying (×) 2 columns may be established, wherein the first column of the matrix may record the characteristic value of the parameter of interest at each sampling point of the signal, i.e., the value of each parameter in the above characteristic information, and the second column of the matrix may record the difference value between the fitted value and the measurement value of the parameter of interest at each sampling point of the signal; or a matrix of 2 rows×n columns may be established, wherein the first row of the matrix may record the characteristic value of the parameter of interest at each sampling point of the signal, and the second row of the matrix may record the difference value between the fitted value and the measurement value of the parameter of interest at each sampling point of the signal, n represents the number of characteristic values; next, the characteristic values and the difference values in the matrix may be used as the abscissa and the ordinate, respectively, to generate the difference distribution diagram of the parameter of interest in each signal segment under each fitting model, or characteristic values may be firstly ranked according to their magnitudes, and then the difference distribution diagram of the parameter of interest in each signal segment under each fitting model may be generated based on the ranking sequence; and finally, the fitting model corresponding to the smallest difference distribution in the difference distribution diagram may be determined as the final fitting model for the respective signal segment.

It should be noted that the final fitting model may be one or more of the plurality of the fitting models. The final fitting models for the respective signal segments may be the same or different from each other.

Figure 4A:
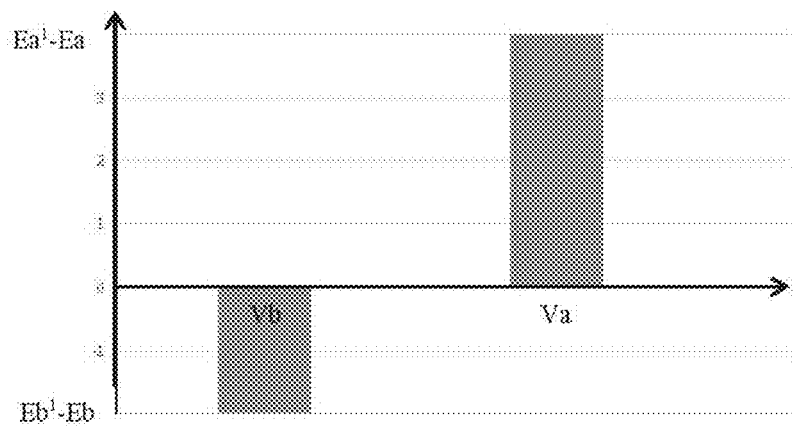
FIG. 4(a) is a histogram of the energy difference distribution of electrical pulse signals a and b under the four-point linear and five-point exponential fitting model.
Figure 4B:
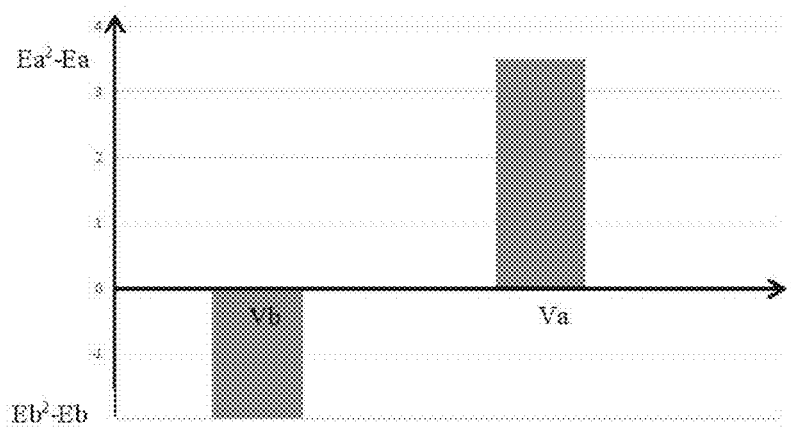
FIG. 4(b) is a histogram of the energy difference distribution of electrical pulse signals a and b under the eight-point double exponential fitting model.
Figure 4C:
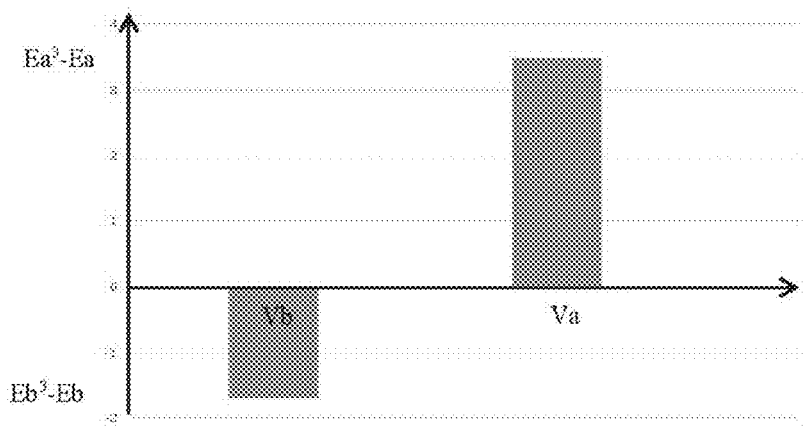
FIG. 4(c) is a histogram of the energy difference distribution of electrical pulse signals a and b under the graph fitting model.

For example, FIGS. 4(a) to 4(c) show histograms of the energy difference distribution of electrical pulse signals a and b under three different fitting models, i.e., the four-point linear and five-point exponential fitting model, the eight-point double exponential fitting model and the graph fitting model, respectively. Wherein, $E_a$ and $E_b$ respectively represent the measurement values of the energy of the electrical pulse signals a and b, $E_a^1$, $E_a^2$ and $E_a^3$ respectively represent the fitted values of the energy of the electrical pulse signal a under the above three fitting models, $E_b^1$, $E_b^2$, and $E_b^3$ respectively represent the fitted values of the energy of the electrical pulse signal b under the above three fitting models, and $V_a$ and $V_b$ respectively represent the amplitudes (i.e., voltages) of the electrical pulse signals a and b extracted from the fitted curve. As shown in the three figures, it can be seen that for the electrical pulse signal a, the energy difference value under either of the eight-point double exponential fitting model and the graph fitting model is relatively small, and thus either of these two fitting models may be selected. For the electrical pulse signal b, there is a minimum energy difference under the graph fitting model, and thus the graph fitting model is the optimal choice.

Figure 5A:
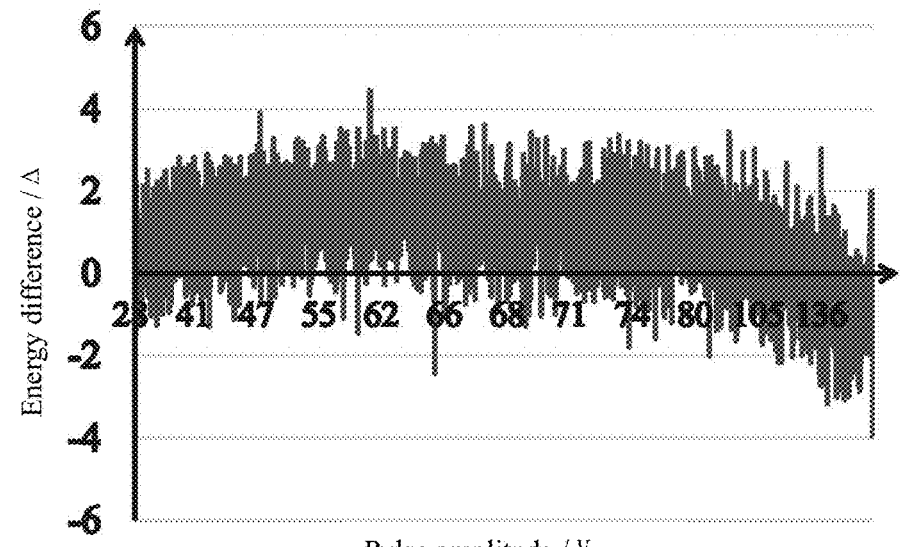
FIG. 5(a) is a diagram of the energy difference distribution of a plurality of electrical pulse signals under the four-point linear and five-point exponential fitting model.
Figure 5B:
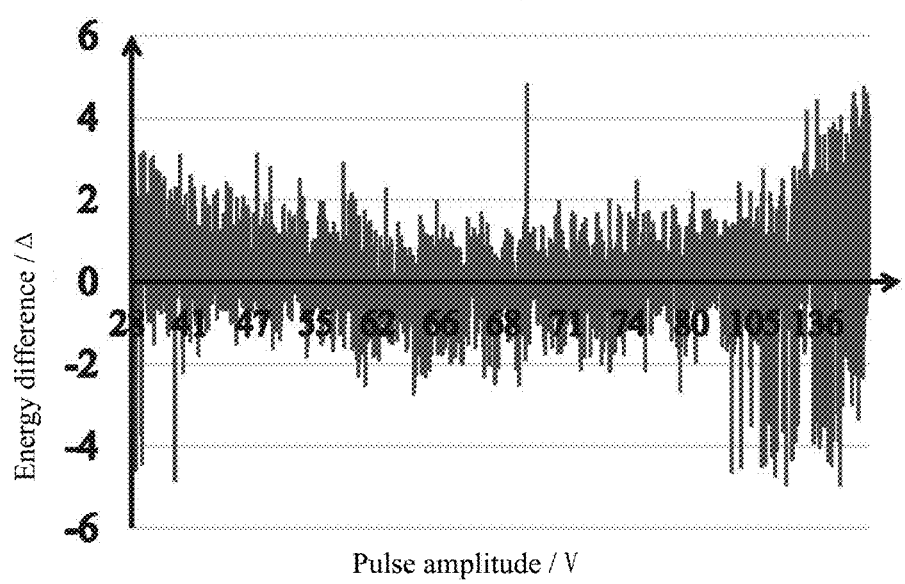
FIG. 5(b) is a diagram of the energy difference distribution of a plurality of electrical pulse signals under the eight-point double exponential fitting model.
Figure 5C:
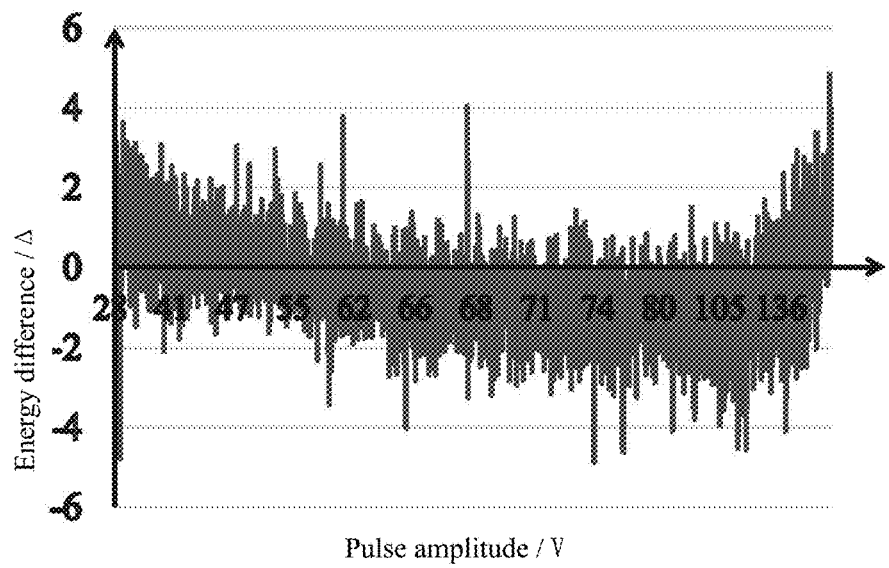
FIG. 5(c) is a diagram of the energy difference distribution of a plurality of electrical pulse signals under the graph fitting model.
Figure 6A:
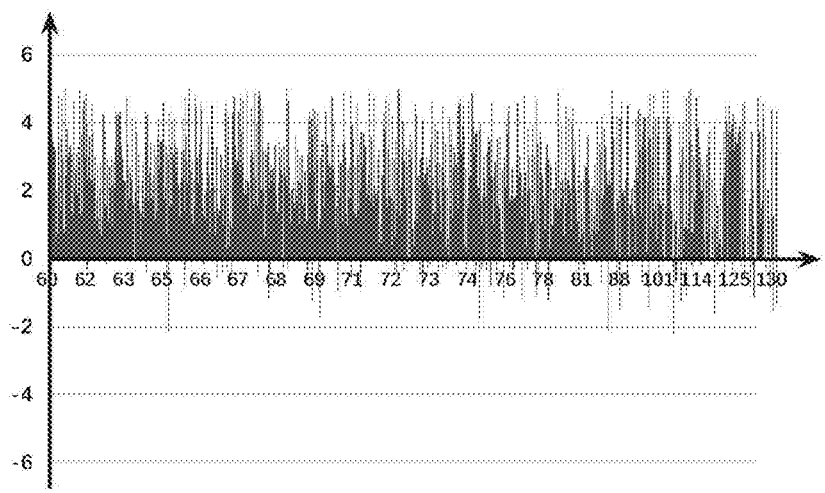
FIG. 6(a) shows a diagram of the energy difference distribution of a plurality of electrical pulse signals under the four-point linear and four-point exponential fitting model within the amplitude range of 60 to 130V.
Figure 6B:
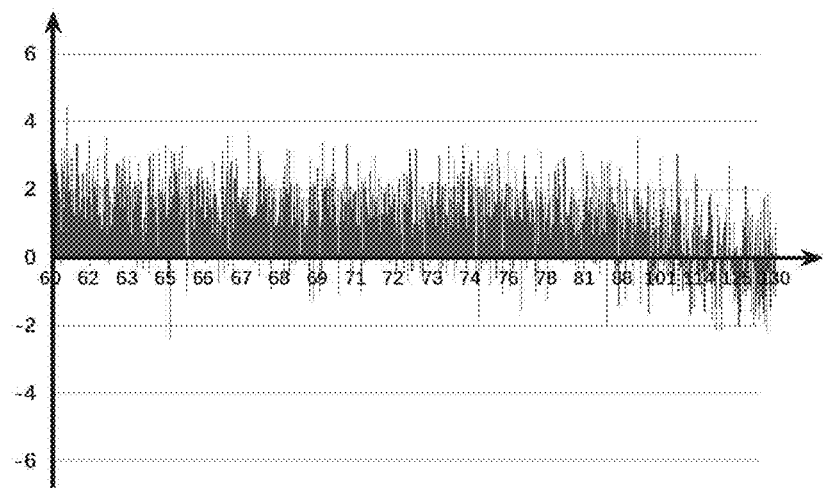
FIG. 6(b) shows a diagram of the energy difference distribution of a plurality of electrical pulse signals under the four-point linear and five-point exponential fitting model within the amplitude range of 60 to 130V.
Figure 6C:
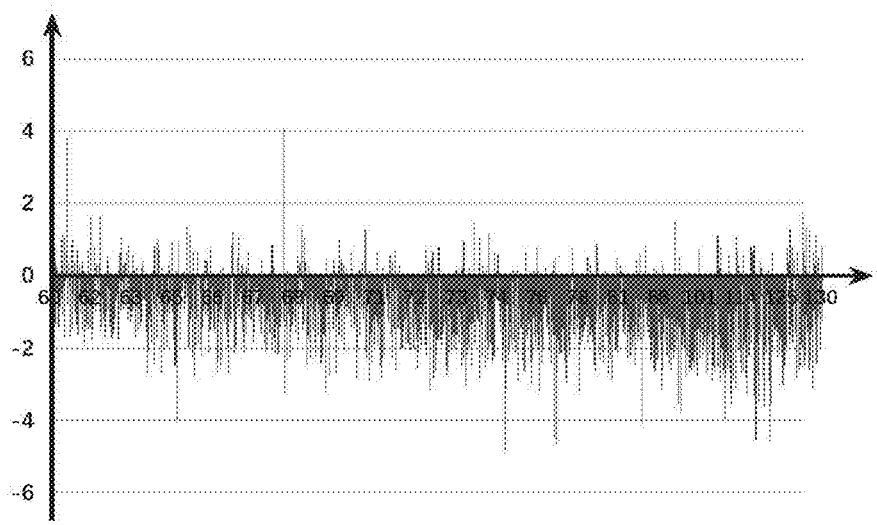
FIG. 6 (c) shows a diagram of the energy difference distribution of a plurality of electrical pulse signals under the graph fitting model, in which the lower curve is fitted by a nine-point double exponential fitting model, within the amplitude range of 60 to 130V.
FIG. 6(d) shows a diagram of the energy difference distribution of a plurality of electrical pulse signals under the graph fitting model, in which the lower curve is fitted by the eight-point double exponential fitting model, within the amplitude range of 60 to 130V.
Figure 6D:
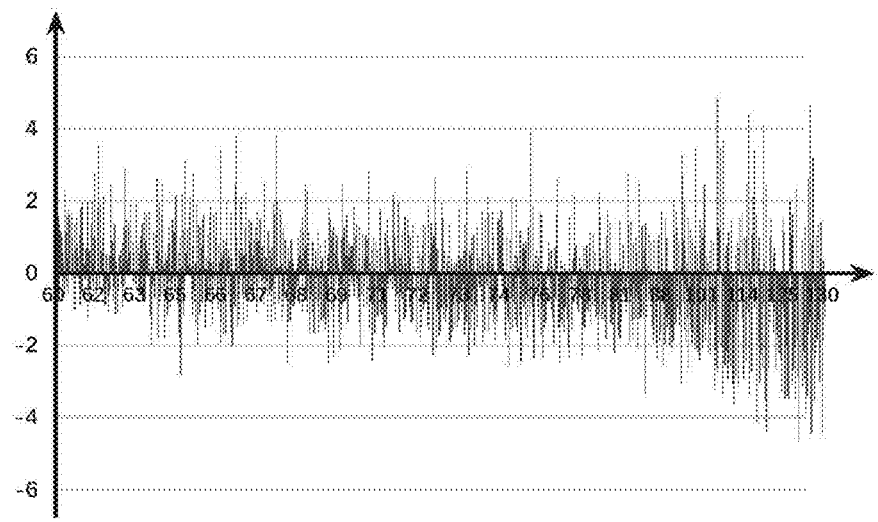

For example, FIGS. 5(a) to 5(c) show diagrams of the energy difference distribution of a plurality of electrical pulse signals under three different fitting models, i.e., the four-point linear and five-point exponential fitting model, the eight-point double exponential fitting model, and the graph fitting model with the lower curve fitted under the eight-point double exponential fitting model, respectively. It can be seen from the three figures that for the electrical pulse signal, there is a smallest energy difference under the graph fitting model within the amplitude range of 62V to 74V, and thus in this case it is preferred to select the graph fitting model for fitting; and there is a smallest energy difference under the four-point linear and five-point exponential fitting model within the amplitude range greater than (>) 136V, and thus in this case it is preferred to select the four-point linear and five-point exponential fitting model for fitting.

For example, FIGS. 6(a) to 6(d) show diagrams of the energy difference distribution of a plurality of electrical pulse signals within the amplitude range of 60V to 130V under four different fitting models, i.e., the four-point linear and four-point exponential fitting model, the four-point linear and five-point exponential fitting model, the graph fitting model with the lower curve fitted under the nine-point double exponential fitting and the graph fitting model with the lower curve fitted under the eight-point double exponential fitting, respectively, wherein, the abscissa represents the amplitude (V) of the electrical pulse signal, and the ordinate represents the energy difference. It can be seen from the four figures that for the electrical pulse signal, there is a smallest energy difference under the graph fitting model with the lower curve fitted under the eight-point double exponential fitting within the amplitude range of 60V to 80V, and thus in this case it is preferred to select the graph fitting model for fitting; and there is a smallest energy difference under the four-point linear and five-point exponential fitting model within the amplitude range of 80V to 130V, and thus in this case it is preferred to select the four-point linear and five-point exponential fitting model for fitting.

From the above, it can be seen that in the embodiments of the disclosure, it may segment the sampled signal according to the characteristic information of the signal, and compare the fitted value of the parameter of interest in each signal segment with the measurement value under a plurality of fitting models, so as to determine a final fitting model for each signal segment based on the comparison result, which reflects that different fitting models can be adopted by considering different characteristics of the signal. Therefore, it may make the subsequent fitting result of the signal more accurate, thereby improving accuracy of the signal reconstruction result and precision of the signal reconstruction. Moreover, it will improve the comparability among the various fitting models and be more intuitional by comparing the fitting models using the form of histograms.

In a further embodiment of the disclosure, the method may further comprise:

S5: storing the determined final fitting model according to the correspondence between each of the signal segments and the final fitting model.

After the final fitting models for all the signal segments are determined, the determined final fitting models may be stored according to the correspondence between the signal segments and the final fitting models, so that they can be directly searched for use later, so as to improve the efficiency of signal reconstruction.

Figure 7:
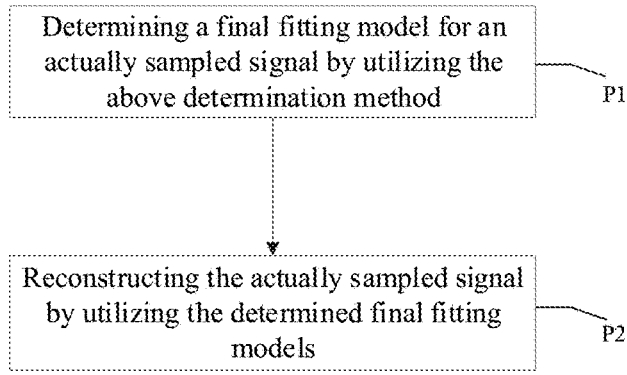
FIG. 7 is a schematic flowchart of a method for reconstructing a signal according to an embodiment of the disclosure.

In the embodiment of the disclosure, a method for reconstructing a signal is provided. As shown in FIG. 7, the method may comprise the following steps:

P1: determining a final fitting model for an actually sampled signal by utilizing the above determination method.

After sampling the acquired signal, it may utilize the above determination method to determine the final fitting model for an actually sampled signal. Reference may be made to the description of FIG. 2 to FIG. 6 with respect to the specific determination process, which will not be elaborated here.

The final fitting model may include at least one of a linear and exponential fitting model, a double exponential fitting model and a graph fitting model.

P2: reconstructing the actually sampled signal by utilizing the determined final fitting models.

After determining the final fitting model for the actual sampled signal, the determined final fitting model is used to fit the sampling points in each signal segment, so as to obtain the fitted curve of the signal, thereby realizing the signal reconstruction.

For example, after determining that the final fitting model for each signal segment is the N-point linear and N-plus-M-point exponential fitting model, it may use N-point linear and N-plus-M-point exponential fitting model to fit sampling points in each signal segment, so as to obtain the fitted curve of the signal. For example, after determining that the final fitting model for the signal is the 2N-plus-M-point double exponential fitting model and the graph fitting model, it may use the two models, respectively to fit sampling points in the respective signal segment, or it may use one of the two models which may involve faster fitting speed or lower energy consumption to fit the sampling points, so as to obtain the fitted curve of the signal. For fitting the sampling points of the signal under the N-point linear and N-plus-M-point exponential fitting model, the 2N-plus-M-point double exponential fitting model and the graph fitting model, reference may be made to the description of the fitting models in step S2, which will not be described here.

By calculating the corresponding data, such as amplitude and time, extracted from the fitted curve, the energy or energy resolution of the signal can be obtained. Reference may be made to the prior art with respect to the calculation method, which will not be elaborated here.

By using the methods for reconstructing the signal according to the embodiments of the disclosure, the accuracy of the signal reconstruction result and precision of the signal reconstruction may be improved.

Examples are given to illustrate the benefits of the above embodiments.

Figure 8:
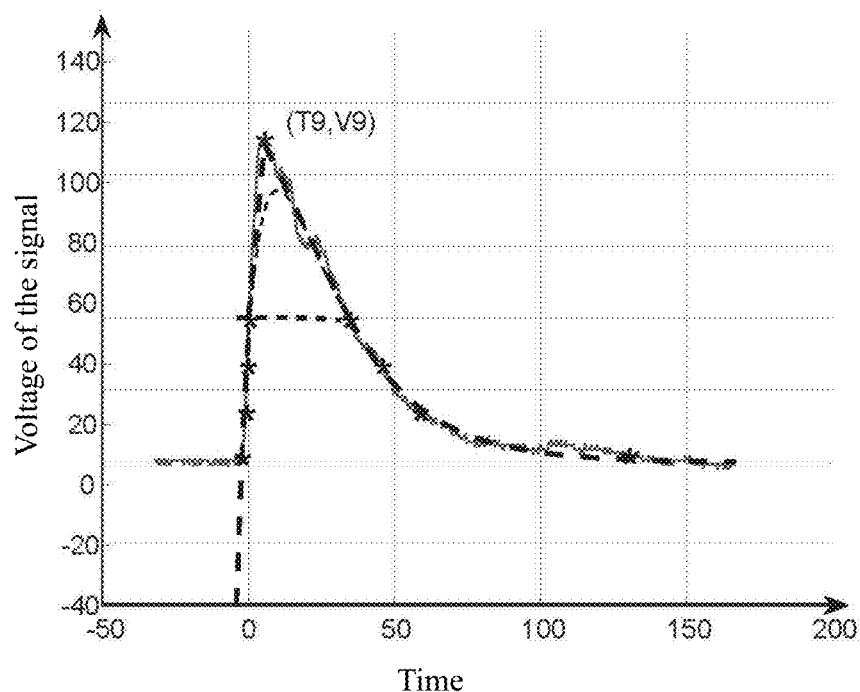
FIG. 8 shows a fitted curve obtained by fitting an electrical pulse signal using the graph fitting model in the disclosure and an actual measurement curve of the electrical pulse signal.
Figure 9:
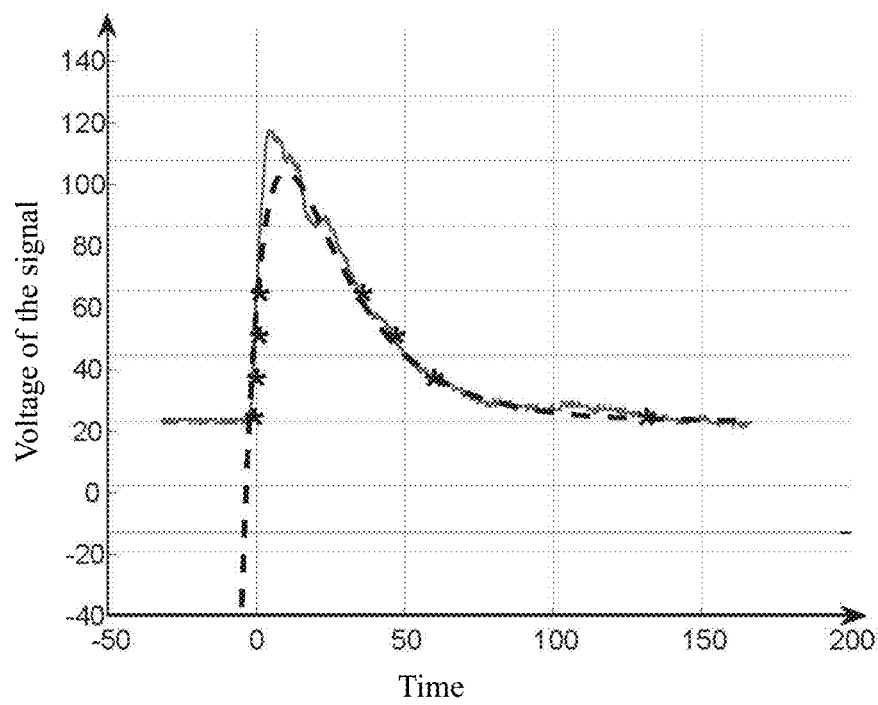
FIG. 9 shows a fitted curve obtained by fitting an electrical pulse signal using the existing eight-point double exponential fitting model and an actual measurement curve of the electrical pulse signal.

FIG. 8 shows a fitted curve obtained by fitting an electrical pulse signal using the graph fitting model in the disclosure, with the lower curve fitted by eight-point double exponential fitting model, and an actual measurement curve of the electrical pulse signal. FIG. 9 shows a fitted curve obtained by fitting an electrical pulse signal using the existing eight-point double exponential fitting model and an actual measurement curve of the electrical pulse signal. Wherein, (T9, V9) represents the coordinates of the $9^{th}$ sampling point, the solid line represents the measurement curve, and the dashed line represents the fitted curve. As shown in the two figures, it can be seen that the fitted curve obtained by using the graph fitting model in the disclosure with the lower curve fitted by eight-point double exponential fitting model is very close to the actual measurement curve, while the curve fitted by using the existing eight-point double exponential fitting model is far from the actual measurement curve. It can be seen that by using the signal reconstruction method of the disclosure, the accuracy of the signal reconstruction result can be improved.

FIG. 10 and FIG. 11 show a fitted curve obtained by using the method for reconstructing a signal according to the embodiment of the disclosure and a fitted curve obtained by using an existing multi-threshold sampling method, respectively. By comparing the two figures with each other, it can be seen that the energy resolution obtained by the method for reconstructing a signal according to the embodiment of the disclosure is about 1.6% lower than the energy resolution obtained by the existing multi-threshold sampling method, which indicates an improvement of the energy precision. By using the method for reconstructing the signal according to the embodiment of the disclosure, moreover, it may identify a photoelectric peak appearing at around 1274 Key, which however is totally unidentifiable by using the existing multi-threshold sampling method. The ability of identifying photoelectric peaks is important for distinguishing different nuclides. It can be seen that, by using the method for reconstructing the signal according to the embodiment of the disclosure, the ability of identifying photoelectric peaks may be improved, which helps to distinguish different nuclides.

In the embodiment of the disclosure, another method for reconstructing a signal is provided. As shown in FIG. 12, the method may comprise the following steps:

P1': comparing an actually sampled signal with a reference signal, a final fitting model for which is determined by utilizing the above determination method, to determine a final fitting model for the actually sampled signal.

After sampling the acquired signal, it may compare the actually sampled signal with the reference signal, the final fitting model for which is determined by utilizing the above determination method. It may search for the reference signal that has the same or similar characteristic information with the actually sampled signal by using the characteristic information of the signal, for example, amplitude, time, rising time of the rising edge, rising slope or the like. After the reference signal is searched out, it may search for the final fitting model for the reference signal according to the correspondence between the reference signal and its final fitting model, and determine the searched final fitting model for the reference signal as the final fitting model for the actually sampled signal. Reference may be made to the description of FIG. 2 to FIG. 6 with respect to the specific determination process of the final fitting model for the reference signal, which will not be elaborated here.

The final fitting model may include at least one of linear and exponential fitting model, double exponential fitting model and graph fitting model.

P2': reconstructing the actually sampled signal by utilizing the determined final fitting model.

For details of this step, reference may be made to the above step P2, which will not be elaborated here.

Figure 13:
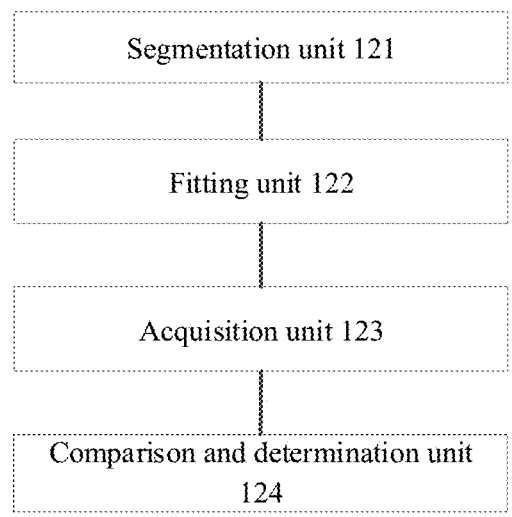
FIG. 13 shows a device for determining a fitting model for a signal according to an embodiment of the disclosure.

In the embodiment of the present disclosure, a device for determining fitting model for a signal is provided. As shown in FIG. 13, the device may comprise:

a segmentation unit 121 that may be configured to segment a sampled signal based on collected characteristic information of the signal to obtain a plurality of signal segments;

a fitting unit 122 that may be configured to fit sampling points in each of the signal segments using a plurality of fitting models;

an acquisition unit 123 that may be configured to acquire fitted values for a parameter of interest in the plurality of signal segments based on fitting results; and a comparison and determination unit 124 that may be configured to sequentially compare each of the fitted values for the parameter of interest under each of the fitting models with an acquired measurement value for the parameter of interest, and to determine a final fitting model for reconstructing the signal among the plurality of the fitting models based on comparison results.

For the details of the above-mentioned units, reference may be made to the method embodiments as shown in FIG. 2, which will not be elaborated here.

By utilizing the above-mentioned device according to the embodiments of the disclosure, the purpose for improving the precision of reconstructing the signal subsequently can be achieved. Moreover, it also can improve the comparability among the various fitting models and be more intuitional.

Figure 14:
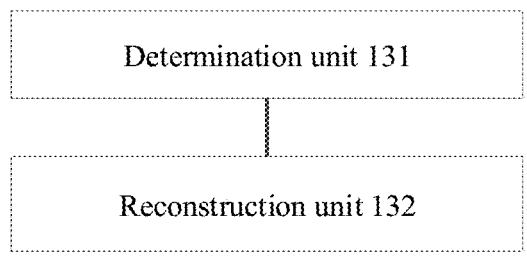
FIG. 14 shows a device for reconstructing a signal according to an embodiment of the disclosure.

In the embodiment of the present disclosure, a device for reconstructing a signal is provided. As shown in FIG. 14, the device may comprise:

a determination unit 131 that may be configured to determine a final fitting model for an actually sampled signal by utilizing the above determination method;

a reconstruction unit 132 that may be configured to reconstruct the actually sampled signal by utilizing the determined final fitting model.

For the details of the above-mentioned units, reference may be made to the method embodiment as shown in FIG. 7, which will not be elaborated here.

Figure 15:
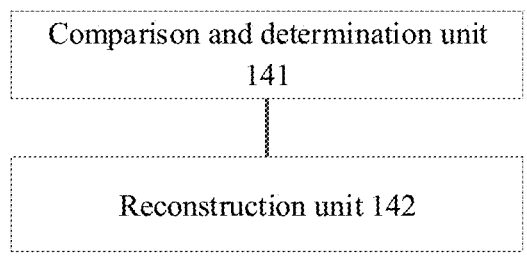
FIG. 15 shows another device for reconstructing a signal according to an embodiment of the disclosure.

In the embodiment of the present disclosure, another device for reconstructing a signal is provided. As shown in FIG. 15, the device may comprise:

a comparison and determination unit 141 that may be configured to compare an actually sampled signal with a reference signal, the final fitting model for which is determined by utilizing the above determination method, to determine a final fitting model for the actually sampled signal; and a reconstruction unit 142 that may be configured to reconstruct the actually sampled signal by utilizing the determined final fitting model.

For the details of the above-mentioned units, reference may be made to the method embodiment as shown in FIG. 12, which will not be elaborated here.

By utilizing the above-mentioned device according to the embodiments of the disclosure, the purpose for improving the precision of reconstructing the signals and thus the accuracy of the reconstruction results can be achieved.

It should be noted that the functions implemented by the units in the above-mentioned devices may also be implemented by executing instructions stored in a memory by a processor in a computer.

It should be noted that the above-mentioned methods and devices according to the embodiments of the disclosure are not just limited to be applied in the fields of PET, multi-voltage threshold sampling (Multi-Voltage Threshold, abbr. MVT) or the like, and may also be applied to any field that requires signal reconstruction.

The devices, units or the like described in the above embodiments may be specifically implemented by computer chips and/or entities, or implemented by products with specific functions. For the convenient purpose, description is made respectively of different functional units of the devices. Of course, when implementing the disclosure, the functions of the individual units may be embodied in the same one or more computer chips.

Although the method steps described in the above-mentioned embodiments or flowcharts are provided in the disclosure, more or fewer steps may be included in the methods with conventional or routine work. The execution order of steps, in which there is no necessary causal relationship logically, is not limited to that provided in the embodiments in the disclosure.

The various embodiments in this specification are described in a progressive manner with the same or similar parts to be referred across the various embodiments, while the description of each embodiment focuses on the differences from other embodiments.

The above-mentioned embodiments are described to facilitate those skilled in the art to understand and practice the disclosure. It is also apparent to those skilled in the art to make various modifications to these embodiments and apply the general principles described herein to other embodiments without creative work. Therefore, the disclosure is not limited to the above-mentioned embodiments, and improvements and modifications made by those skilled in the art according to the disclosure without departing from the scope of this disclosure should fall within the protection scope of the disclosure.

What is claimed is:

1. A method for determining a fitting model for a signal, the method comprising:
   segmenting a sampled signal based on collected characteristic information of the signal to obtain a plurality of signal segments;
   fitting sampling points in the plurality of signal segments using a plurality of fitting models;
   acquiring fitted values for a parameter of interest in each signal segment of the plurality of signal segments based on fitting results;
   sequentially comparing each of the fitted values for the parameter of interest under each of the fitting models with an acquired measurement value for the parameter of interest; and
   determining a final fitting model for reconstructing the sampled signal among the plurality of the fitting models based on comparison results.

2. The method according to claim 1, wherein the signal includes an electrical signal that includes an electrical pulse signal from a radiation detector, an optical signal, or a sound signal.

3. The method according to claim 1, wherein the characteristic information of the signal includes at least one of amplitude, rising slope, rising time, falling slope, or falling time of the signal.

4. The method according to claim 1, wherein the plurality of the fitting models includes: at least one of a linear and exponential fitting model, a double exponential fitting model, or a graph fitting model.

5. The method according to claim 4, wherein the graph fitting model comprises a triangle fitting model adopted at an upper portion with respect to a sampling threshold, and the linear and exponential fitting model or the double exponential fitting model adopted at a lower portion with respect to the sampling threshold, wherein the linear and exponential fitting model includes an N-point linear and N-point exponential fitting model or and an N-point linear and N-plus-M-point exponential fitting model, wherein the double exponential fitting model includes a 2N-point double exponential fitting model or a 2N-plus-M-point double exponential fitting model, wherein N is a positive integer greater than 1 and M is a positive integer greater than or equal to 1.

6. The method according to claim 1, wherein the parameter of interest includes an energy, a time, an energy resolution, or a time resolution of the signal.

7. The method according to claim 1 wherein determining the final fitting model comprises:
   sequentially calculating difference value between each of the fitted values for the parameter of interest in each signal segment of the plurality of signal segments under each of the fitting models and the measurement value for the parameter of interest, and determining the final fitting model for reconstructing each signal segment of the plurality of signal segments among the plurality of the fitting models based on the difference value.

8. The method according to claim 7, wherein determining the final fitting model comprises:
   determining, among the plurality of the fitting models, a fitting model under which there is a smallest absolute difference value for the parameter of interest in each signal segment of the plurality of signal segments, as the final fitting model for each signal segment of the plurality of signal segments.

9. The method according to claim 1, further comprising:
   storing the determined final fitting model according to a correspondence between each signal segment of the plurality of signal segments and the final fitting model.

10. A method for reconstructing a signal, the method comprising:
    segmenting an actually sampled signal based on collected characteristic information of the actually sampled signal to obtain a plurality of signal segments;
    fitting sampling points in the plurality of signal segments using a plurality of fitting models;
    acquiring fitted values for a parameter of interest in each signal segment of the plurality of signal segments based on fitting results;
    sequentially comparing each of the fitted values for the parameter of interest under each of the fitting models with an acquired measurement value for the parameter of interest;
    determining a final fitting model for reconstructing the actually sampled signal among the plurality of the fitting models based on comparison results;
    reconstructing the actually sampled signal by utilizing the determined final fitting model.

11. A method for reconstructing a signal, the method comprising:
    comparing an actually sampled signal with a reference signal to determine a final fitting model for the actually sampled signal, wherein a final fitting model for the reference signal is determined by:
       segmenting the reference signal based on collected characteristic information of the reference signal to obtain a plurality of signal segments;
       fitting sampling points in the plurality of signal segments using a plurality of fitting models;
       acquiring fitted values for a parameter of interest in each signal segment of the plurality of signal segments based on fitting results;
       sequentially comparing each of the fitted values for the parameter of interest under each of the fitting models with an acquired measurement value for the parameter of interest; and
       determining a final fitting model for reconstructing the reference signal among the plurality of the fitting models based on comparison results; and
    reconstructing the actually sampled signal by utilizing the determined final fitting model.

12. The method according to claim 11, wherein comparing the actually sampled signal with the reference signal comprises:
    searching for the reference signal having the same or similar characteristic information with the actually sampled signal by utilizing the characteristic information of the actually sampled signal; and
    after the reference signal is determined, searching for the final fitting model for the reference signal according to a correspondence between the reference signal and the final fitting model, and determining the final fitting model for the reference signal as a final fitting model for the actually sampled signal.

13. A device for determining a signal fitting model, the device comprising:
    a segmentation unit configured to segment a sampled signal based on characteristic information of the sampled signal to obtain a plurality of signal segments;
    a fitting unit configured to fit sampling points in the plurality of the signal segments using a plurality of fitting models;

an acquisition unit configured to acquire fitted values for a parameter of interest in each signal segment of the plurality of signal segments based on fitting results; and a comparison and determination unit configured to sequentially compare each of the fitted values for the parameter of interest under each of the fitting models with an acquired measurement value for the parameter of interest, and to determine a final fitting model for reconstruction of the signal among the plurality of the fitting models based on comparison results.

14. The device according to claim 13, wherein the comparison and determination unit is configured to sequentially calculate difference value between each of the fitted values for the parameter of interest in each signal segment of the signal segments under each of the fitting models and the acquired measurement value for the parameter of interest, and determine the final fitting model for reconstructing each signal segment of the plurality of signal segments among the plurality of the fitting models based on the difference value.

15. The device according to claim 13, further comprising:

a storage unit configured to store the determined final fitting model according to a correspondence between each signal segment of the plurality of signal segments and the final fitting model.

16. A device for reconstructing a signal, the device comprising:

a determination unit configured to determine a final fitting model for an actually sampled signal, wherein the determination unit is further configured to:

segment the actually sampled signal based on collected characteristic information of the actually sampled signal to obtain a plurality of signal segments;

fit sampling points in the plurality of signal segments using a plurality of fitting models;

acquire fitted values for a parameter of interest in each signal segment of the plurality of signal segments based on fitting results;

sequentially compare each of the fitted values for the parameter of interest under each of the fitting models with an acquired measurement value for the parameter of interest; and determine a final fitting model for reconstructing the actually sampled signal among the plurality of the fitting models based on comparison results; and a reconstruction unit configured to reconstruct the actually sampled signal by utilizing the determined final fitting model.

17. A device for reconstructing a signal, the device comprising:

a comparison and determination unit configured to compare an actually sampled signal with a reference signal to determine a final fitting model for the actually sampled signal, wherein a final fitting model for the reference signal is determined by:

segmenting the reference signal based on collected characteristic information of the reference signal to obtain a plurality of signal segments;

fitting sampling points in the plurality of signal segments using a plurality of fitting models;

acquiring fitted values for a parameter of interest in each signal segment of the plurality of signal segments based on fitting results;

sequentially comparing each of the fitted values for the parameter of interest under each of the fitting models with an acquired measurement value for the parameter of interest; and determining a final fitting model for reconstructing the reference signal among the plurality of the fitting models based on comparison results; and a reconstruction unit configured to reconstruct the actually sampled signal by utilizing the determined final fitting model.

18. The device according to claim 17, wherein the comparison and determination unit is configured to:

search for the reference signal having the same or similar characteristic information with the actually sampled signal by utilizing characteristic information of the actually sampled signal, and after the reference signal is determined search for the final fitting model for the reference signal according to a correspondence between the reference signal and the final fitting model for the reference signal, and determine the searched final fitting model for the reference signal as a final fitting model for the actually sampled signal.

19. The method according to claim 7, wherein determining the final fitting model comprises:

determining, among the plurality of the fitting models, the fitting model with a smallest difference distribution for the parameter of interest in each signal segment of the plurality of signal segments, as the final fitting model for each signal segment of the plurality of signal segments.

* * * * *